(12) United States Patent
Teague

(10) Patent No.: US 9,999,753 B2
(45) Date of Patent: Jun. 19, 2018

(54) UROLOGICAL MEDICAL DEVICES HAVING A POROUS MEMBRANE FOR DELIVERY OF UROLOGICALLY BENEFICIAL AGENTS

(75) Inventor: James A. Teague, Spencer, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 614 days.

(21) Appl. No.: 13/477,268

(22) Filed: May 22, 2012

(65) Prior Publication Data

US 2012/0302971 A1  Nov. 29, 2012

Related U.S. Application Data

(60) Provisional application No. 61/489,560, filed on May 24, 2011.

(51) Int. Cl.
*A61M 27/00* (2006.01)
*A61M 25/00* (2006.01)

(52) U.S. Cl.
CPC ........ *A61M 27/008* (2013.01); *A61M 25/007* (2013.01); *A61M 27/002* (2013.01); *A61M 2025/0057* (2013.01); *A61M 2210/1078* (2013.01); *A61M 2210/1082* (2013.01); *A61M 2210/1085* (2013.01)

(58) Field of Classification Search
CPC ........ A61M 2025/0163; A61M 27/002; A61M 27/008; A61M 2210/1078; A61M 25/0017; A61M 2025/0057; A61M 25/007; A61M 2210/1082; A61M 2210/1085; A61M 2210/1089

USPC .. 604/93.01, 175, 264, 523, 288.01, 288.02, 604/288.04

See application file for complete search history.

(56) References Cited

U.S. PATENT DOCUMENTS

| | | | | |
|---|---|---|---|---|
| 4,010,393 | A * | 3/1977 | Lorch et al. | 310/194 |
| 4,673,394 | A * | 6/1987 | Fenton, Jr. | A61M 5/14276 128/912 |
| 4,911,717 | A * | 3/1990 | Gaskill, III | A61F 2/022 604/891.1 |
| 5,141,502 | A * | 8/1992 | Macaluso, Jr. | 604/528 |
| 5,370,613 | A * | 12/1994 | Helmy | 604/288.02 |
| 6,908,447 | B2 * | 6/2005 | McWeeney | A61F 2/0022 604/9 |
| 8,414,656 | B2 * | 4/2013 | Davoudi et al. | 623/23.7 |
| 2003/0171708 | A1 * | 9/2003 | Segura et al. | 604/8 |
| 2006/0253104 | A1 * | 11/2006 | Pandey | A61M 27/008 604/540 |
| 2008/0082154 | A1 * | 4/2008 | Tseng | A61F 2/07 623/1.11 |
| 2008/0234659 | A1 * | 9/2008 | Cheng et al. | 604/523 |
| 2008/0249636 | A1 * | 10/2008 | Deal | A61F 2/04 623/23.66 |
| 2009/0171465 | A1 * | 7/2009 | Bucay-Couto et al. | 623/23.7 |
| 2009/0187254 | A1 * | 7/2009 | Deal et al. | 623/23.7 |
| 2009/0248169 | A1 * | 10/2009 | Li | 623/23.7 |

(Continued)

*Primary Examiner* — Kami A Bosworth
*Assistant Examiner* — Shefali Patel

(57) ABSTRACT

In one aspect, the present invention provides implantable or insertable urological medical devices, which are adapted to deliver one or more urologically beneficial agents in pharmaceutically effective amounts. In one aspect, the invention provides medical devices in which urologically beneficial agents are delivered using a porous membrane.

19 Claims, 3 Drawing Sheets

(56) References Cited

U.S. PATENT DOCUMENTS

2009/0281635 A1* 11/2009 Li et al. .................. 623/23.66
2010/0160848 A1   6/2010 Ostrovsky et al.

* cited by examiner

UROLOGICAL MEDICAL DEVICES HAVING A POROUS MEMBRANE FOR DELIVERY OF UROLOGICALLY BENEFICIAL AGENTS

STATEMENT OF RELATED APPLICATION

This application claims the benefit of U.S. Ser. No. 61/489,560, filed May 24, 2011 and entitled "UROLOGICAL MEDICAL DEVICES HAVING A POROUS MEMBRANE FOR DELIVERY OF UROLOGICALLY BENEFICIAL AGENTS," which is hereby incorporated by reference in its entirety.

FIELD OF THE INVENTION

The present invention relates generally to urological medical devices, and more particularly to implantable or insertable urological medical devices which deliver urologically beneficial agents (also referred to herein as "drugs" and "therapeutic agents").

BACKGROUND OF THE INVENTION

Various urological medical devices have been developed for implantation or insertion into patients. As an example, polymeric ureteral stents are widely used to facilitate drainage in the upper urinary tract (e.g., drainage from the kidney to the bladder). They are used, for example, in post endourological procedures to act as a scaffold in the event of ureteral obstruction secondary to the procedure. Ureteral stents are also used as palliative devices to provide patency in the presence of congenital defects, strictures or malignancies, as well as in other instances where ureteral obstruction may occur. A schematic illustration of a ureteral stent 10 in accordance with the prior art is illustrated in FIGS. 1A and 1B. The stent 10 has a proximal end 10p and a distal end 10d. It is a tubular polymeric extrusion having a shaft 12, a distal renal retention structure (e.g., renal coil or "pigtail" 14), and a proximal retention structure (e.g., bladder coil or "pigtail" 16). These retention structures prevent upward migration of the stent toward the kidney or downward migration of the stent toward the bladder. The shaft 12 in cross-section is a single extruded layer as seen from FIG. 1B, which is taken along line b-b of FIG. 1A. Once properly deployed in the ureter, the stent 10 provides ureteral rigidity and allows the passage of urine. The stent 10 of FIGS. 1A and 1B is further provided with the following features: (a) a tapered tip 11, to aid insertion, (b) a central lumen 10c, (c) multiple side ports 18 (one numbered), which are arranged in a spiral pattern down the length of the body to promote drainage, (d) graduation marks 25 (one illustrated) for visualization by the physician to know when the appropriate length of stent has been inserted into the ureter, and (e) a suture 22, which aids in positioning and withdrawal of the stent. During placement, such ureteral stents 10 are typically placed over a urology guide wire, through a cystoscope and advanced into position. Once the distal end of the stent is advanced into the kidney/renal calyx, the guide wire is removed, allowing the coils 14, 16 to form in the kidney 19 and bladder 20, as shown in FIG. 2. As shown in FIG. 2, the stent 10 extends through the ureteral orifice 21a and into the bladder 20. For clarity, the ureter entering bladder 20 through the opposite ureteral orifice 21b is not shown.

SUMMARY OF THE INVENTION

The present invention provides implantable or insertable urological medical devices which deliver one or more urologically beneficial agents.

In one aspect, the invention provides medical devices in which urologically beneficial agents are delivered using a porous membrane.

Advantages of the present invention include the fact that urological medical devices may be provided which locally deliver urologically beneficial agents, thereby avoiding the need for systemic drug administration, which typically requires higher quantities of drug to be efficacious.

Another advantage of the present invention is that urological medical devices may be provided, which act as a delivery platform for essentially any agent a physician or other caregiver may wish to administer.

These and other aspects, embodiments and advantages of the present invention will become immediately apparent to those of ordinary skill in the art upon review of the Detailed Description and any claims to follow.

DETAILED DESCRIPTION OF THE INVENTION

Figure 1A:
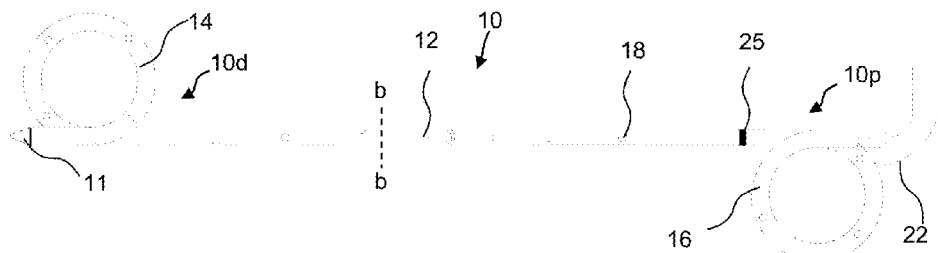
FIG. 1A is a schematic representation of a ureteral stent, according to the prior art.
Figure 1B:
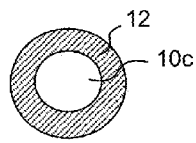
FIG. 1B is a cross-section taken along plane B-B of FIG. 1A.
Figure 2:
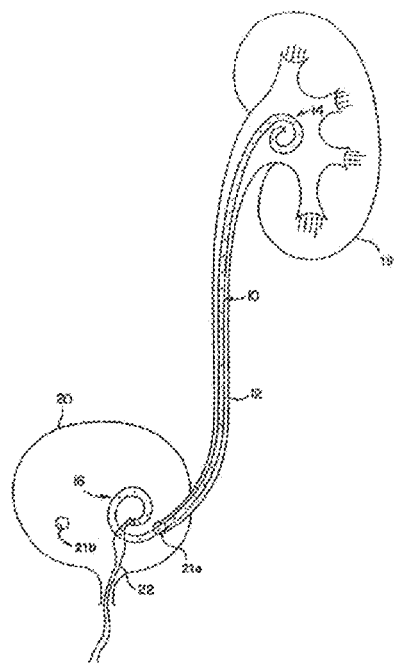
FIG. 2 shows a ureteral stent like that of FIG. 1A as positioned within the body.

A more complete understanding of the present invention is available by reference to the following detailed description of numerous aspects and embodiments of the invention. The detailed description of the invention which follows is intended to illustrate but not limit the invention.

The present invention provides implantable or insertable urological medical devices which deliver one or more urologically beneficial agents in the urinary tract of a subject in effective amounts. In one aspect, the invention provides medical devices in which urologically beneficial agents are delivered using a porous membrane.

For example, as discussed in more detail below, in certain embodiments, implantable or insertable urological devices are provided which comprise (a) a porous membrane delivery element with an internal delivery lumen and (b) an injection port for introduction of a urologically beneficial agent into the delivery lumen. Upon implantation or insertion of the device in the urinary tract of a subject, the urologically beneficial agent is released from the delivery lumen into the subject through pores in the porous membrane delivery element.

Preferred subjects (also referred to as "patients") are vertebrate subjects, more preferably mammalian subjects, including human subjects, pets and livestock.

As used herein, "proximal end" refers to the end of the object that lies closest to the urethral exit (downstream) in the urinary tract, and "distal end" refers to the end of an implanted or inserted object that lies furthest from the urethral exit (upstream) in the urinary tract.

Porous membranes for use in the present disclosure may be formed from a variety of materials. In certain embodiments, the porous membranes are formed from a polymeric material, numerous examples of which are set forth below. In certain particularly preferred embodiments, the membrane is formed from expanded polytetrafluoroethylene (ePTFE) or polyethylene terephthalate glycol (PETG).

Membrane pore size will vary with the desired delivery rate and will typically range from 0.1 to 10 µm, for example from 0.1 to 0.2 to 0.5 to 1 to 2 to 5 to 10 µm, preferably about 1 µm.

The porous membrane may be rigid or flexible. Membrane thickness will vary widely, but typically ranges from 10 to 500 µm, for example, from 10 to 20 to 50 to 100 to 200 to 500 µm in thickness. In certain embodiments (e.g., where the membrane is a polymeric membrane having a thickness less than 50 µm, more broadly less than 100 µm, among other possibilities), the porous membrane has a cloth-like flexibility.

Delivery rate will depend upon a number of variables including the membrane pore size and the area of the membrane that is contacts the urologically beneficial agent. The delivery rate may also depend upon other factors including the concentration of the urologically beneficial agent, for example, in instances where the urologically beneficial agent is introduced as a liquid solution or dispersion.

In certain embodiments, the urological medical devices exhibit an extended delivery profile. In certain other embodiments, the urological medical devices exhibit a rapid delivery profile.

As used herein, a "rapid delivery profile" is a delivery profile in which a majority of the urologically beneficial agent is delivered (e.g., more than 50% is delivered) shortly after implantation or insertion. For example, a majority of the urologically beneficial agent may be delivered within 1 day, within 12 hours, within 6 hours, within 3 hours or even within 1 hour of implantation or insertion.

As used herein an "extended delivery profile" is meant a delivery profile by which an effective amount of urologically beneficial agent continues to be delivered at least 7 days after device implantation or insertion, for example after 7 days, after 14 days, after 1 month, after 2 months, or after 3 months or more.

In some embodiments, devices are provided which are adapted to be advanced over a guide wire and/or advanced through a channel, for example, a channel associated with a guide catheter or scope.

In some embodiments, devices are provided which comprise one or more elements that take on a particular beneficial shape in vivo, for example, upon removal of a guide wire or upon emergence from a channel (e.g., due to elastic rebound of the material) or upon application of an external stimulus such as heat or light (e.g., where a shape memory material such as a shape memory polymer is employed). For example, the device may comprise one or more retention elements which take on a non-linear form. Such constructions allow the medical device to be held in place in the urinary tract, for example, by forming a coil or other non-linear retention element shape in the kidney (e.g., in the renal calyx and/or renal pelvis), the bladder, or both.

Urologically beneficial agents for use in the medical devices of the invention include antimicrobial agents, agents that reduce pain and/or discomfort (also referred herein as "discomfort reducing agents"), anti-cancer drugs, and combinations thereof.

The term "antimicrobial agent" as used herein means a substance that kills microbes and/or inhibits the proliferation and/or growth of microbes, particularly bacteria, fungi and yeast. Antimicrobial agents, therefore, include biocidal agents and biostatic agents as well as agents that possess both biocidal and biostatic properties. In the context of the present invention, the antimicrobial agent kills microbes and/or inhibits the proliferation and/or growth of microbes on and around the surfaces of the implanted or inserted urological medical device, and can therefore inhibit biofilm formation (encrustation) in some cases.

Antimicrobial agents may be selected, for example, from triclosan, chlorhexidine, nitrofurazone, benzalkonium chlorides, silver salts and antibiotics, such as rifampin, gentamicin and minocycline, and combinations thereof, among others.

Further antimicrobial agents may be selected, for example, from suitable members of the following: the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., loracarbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.), among others, as well as combinations and pharmaceutically acceptable salts, esters and other derivatives of the same.

Discomfort reducing agents include antispasmodic agents, alpha-adrenergic blockers, corticosteroids, narcotic analgesic agents, non-narcotic analgesic agents, local anesthetic agents, and combinations thereof.

Antispasmodic agents may be selected, for example, from suitable members of the following: alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenyl-propylamine, tropenzile, trospium chloride, and xenylropium bromide, among others, as well as combinations and pharmaceutically acceptable salts, esters and other derivatives of the same.

Examples of alpha-adrenergic blockers for use in the present invention may be selected from suitable members of the following: alfuzosin, amosulalol, arotinilol, dapiprazole, doxazosin, ergoloid mesylates, fenspiride, idazoxan, indoramin, labetalol, manotepil, naftopidil, nicergoline, prazosin, tamsulosin, terazosin, tolazoline, trimazosin, and yohimbine, among others, as well as combinations and pharmaceutically acceptable salts, esters and other derivatives of the same. Of these, tamsulosin, alfuzosin, doxazosin, prazosin, tamsulosin and terazosin are alpha-1-adrenergic blockers, of which tamsulosin and alfuzosin are selective alpha-1-adrenergic blockers.

Examples of corticosteroids for use in the present invention may be selected from suitable members of the following: betamethasone, cortisone, dexamethasone, deflazacort, hydrocortisone, methylprednisolone, prednisolone, prednisone and triamcinolone, among others, as well as combinations and pharmaceutically acceptable salts, esters and other derivatives of the same.

Examples of narcotic analgesic agents for use in the present invention may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present invention may be selected from suitable members of the following: analgesic agents such as acetaminophen, and non-steroidal anti-inflammatory drugs such as aspirin, diflunisal, salsalate, ibuprofen, ketoprofen, naproxen, indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present invention may be selected from suitable members of the following: benzocaine, cocaine, lidocaine, mepivacaine, and novacaine, among others, as well as combinations and pharmaceutically acceptable salts, esters and other derivatives of the same.

Examples of anticancer drugs include alkyating agents such as mechlorethamine, nitrosoureas (carmustine, lomustine), melphalan, cyclophosphamide, busulfan and procarbazine, antimetabolites such as methotrexate, 6-thioguanine, 5-fluorouracil, 6-mercaptopurine, cytosine arabinoside, gemcitabine, fludarabine and capecitabine, antimitotics such as vincristine, vinblastine, paclitaxel and docetaxel, hormones such as estrogens, prednisone, goserelin, anti-estrogen (tamoxifen), flutamide, leuprolide, immunosuppressives such as azathioprine, tacrolimus (FK506), cyclosporin a, natural products such as dactinomycin, bleomycin, camptothecin and analogs (e.g., irinotecan and topotecan), daunorubicin, mitomycin C, doxorubicin, etoposide (VP-16), and other agents such as hydroxyurea, asparaginase, amsacrine, cisplatin, carboplatin, mitoxantrone and imatinib.

Many of the above and other urologically beneficial agents may be found, for example, in *The Merck Index*, 14$^{th}$ Edition, M. J. O'Neil, Senior Editor, published by Merck Research Laboratories, 2006.

Urologically beneficial agents may be provided in a liquid composition, for instance, as a solution or dispersion within a suitable liquid, which may comprise water and/or an organic solvent.

The urological medical devices of the invention may also contain one or more optional supplemental agents such as imaging agents. For example, x-ray based fluoroscopy is a diagnostic imaging technique that allows real-time patient monitoring of motion within a patient. To be fluoroscopically visible, devices and/or compositions are typically rendered more absorptive of x-rays than the surrounding tissue. In various embodiments of the invention, this is accomplished by the use of radio-opaque agents. Examples of radio-opaque agents for use in connection with x-ray fluoroscopy include metals, metal salts and oxides (particularly bismuth salts and oxides), and iodinated compounds, among others. More specific examples of such radio-opaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others.

In many embodiments, medical device components, including the porous membrane, the injection port and/or any retention element, are at least partially formed from polymeric materials. Polymeric materials are materials that comprise one or more polymers. Polymers for use in the medical devices of the invention may be selected, for example, from suitable members of the following, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyetherblock co-polyamide polymers (e.g., Pebax® resins), polycaprolactams and polyacrylamides; polycarbonates; polyacrylonitriles; polyvinylpyrrolidones; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2- one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers; as well as blends and further copolymers of the above.

As indicated above, the present invention provides implantable or insertable urological medical devices which deliver effective amounts of one or more urologically beneficial agents in the urinary tract of a subject. In one aspect, the invention provides medical devices by which urologically beneficial agents are delivered using a porous membrane.

In certain preferred embodiments, the porous membrane forms a porous membrane delivery element with an internal delivery lumen. A urologically beneficial agent may be introduced into the internal delivery lumen of the porous membrane delivery element, which acts as a temporary reservoir for the urologically beneficial agent. The urologically beneficial agent is delivered from the internal delivery lumen into the urinary tract via pores in the membrane.

In certain embodiments, the pores in the membrane may initially be blocked (e.g., covered and/or at least partially filled) by a biodisintegrable blocking material (e.g., comprising a biodegradable polymer, a biodissolvable polymer, a biodissolvable small molecule such as sugar or salt, etc.) in order to delay the delivery of the urologically beneficial agent.

Porous membrane delivery elements with internal delivery lumens may be formed in a wide variety of shapes. For instance, a porous membrane may be used to form non-elongate (e.g., hollow spherical, etc.) porous membrane delivery elements or elongate (e.g., tubular, etc.) porous membrane delivery elements.

The delivery devices described herein may comprise an injection port, which provides access to the internal delivery lumen of the porous membrane delivery element. For example, a self-closing needle injection port may be employed for this purpose. A self-closing needle injection port may be formed, for example, from a suitable polymeric material through which an injection needle can be passed, for instance, a suitable natural or synthetic rubber material or another suitable elastomeric material (e.g., selected from the polymers listed above). A common example of a self-closing needle injection port is a natural or synthetic rubber septum.

Figure 5:
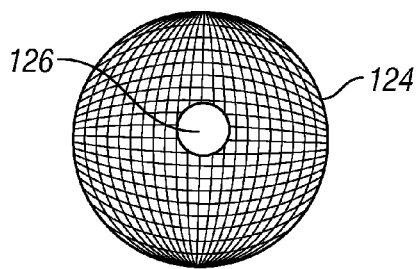
FIGS. 5 and 6 are schematic illustrations of medical devices in accordance with still other embodiments of the invention.

Referring now to FIG. 5, a schematic illustration of a medical device is shown which includes a porous membrane in the form of a spherical porous membrane delivery element 124, which is hollow, thereby forming an interior delivery lumen. The device also includes a self-closing needle injection port 126 that provides access to the interior delivery lumen. The interior delivery lumen is sealed off from the exterior environment, except for the pores in the porous membrane delivery element 124, through which the injected material is released.

As noted above, in certain embodiments, a device is provided which comprises an elongate porous membrane delivery element. For instance, an elongate porous membrane delivery element may be formed using a porous membrane that is in the form of a tube with a closed end (which may also be referred to herein as a "sock" or "sack"). The elongate porous membrane delivery element may be constant in width along its length or may vary in width along its length, for instance, undulating in width along its length, decreasing in width along its length, increasing in width along its length, and so forth. A tubular membrane with a closed end may be created, for example, as a result of the membrane formation process (e.g., by virtue of a molding process, such as blow molding, injection molding, etc.) or by sealing an open end of a tubular porous membrane (e.g., by solvent bonding, heat bonding, adhesive bonding, etc.). The open end opposite the closed end may be placed in fluid communication with an injection port, for example, by attaching/sealing the injection port directly to the tubular membrane or by attaching/sealing a receiving structure that comprises an injection port to the tubular membrane. In either case, the injection port or the receiving structure is attached such that the internal delivery lumen is sealed from the exterior environment. Consequently, urologically beneficial agent introduced into the device is forced to exit the device through the pores of the porous membrane delivery element, which regulates the release of the urologically beneficial agent.

Figure 6:

FIG. 6 is a schematic illustration of a device in which an injection port 126 (e.g., a rubber septum) is attached and sealed to the open end of an elongate hollow porous membrane 124. FIG. 6 is thus analogous to FIG. 5, except that an elongate porous membrane delivery element is substituted for the spherical porous membrane delivery element.

In certain embodiments, a porous membrane delivery element is attached to a bladder or kidney retention element (e.g., an element which can be changed in shape once positioned in the kidney or bladder to retain the element in the kidney or bladder, for instance, a coil, balloon, etc.).

In certain embodiments, an open end of an elongate porous membrane delivery element is attached and sealed to an agent receiving structure that includes an injection port and is configured such that a urologically beneficial agent can be introduced into an interior receiving lumen of the agent receiving structure via the injection port. Further, the interior receiving lumen of the agent receiving structure is in fluid communication with the internal delivery lumen of the elongate porous membrane delivery element. In certain instances, the agent receiving structure may also be configured to act as a retention element, for example, being formed in the shape of a coil.

The agent receiving structure and/or retention element may be formed from a variety of materials and is typically formed from a polymeric material such as those set forth above, for example, polyurethanes, polyether-block-polyamide copolymers (e.g., Pebax® resins), silicones, and ethylene-vinyl acetate copolymers, among others.

A porous membrane delivery element may be attached and sealed to an agent receiving structure and/or retention element, for example, by solvent bonding, heat bonding or adhesive bonding, among other techniques.

Figure 3A:
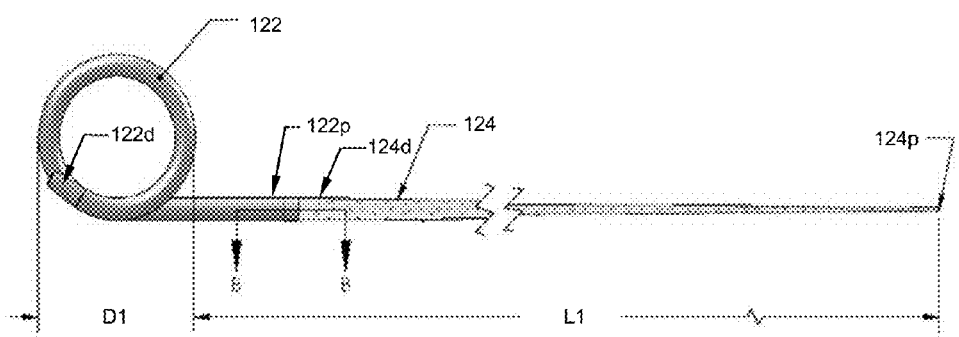
FIG. 3A is an illustration of a medical device in accordance with an embodiment of the invention.

Turning again to the drawings, FIG. 3A is an illustration of a medical device in accordance with an embodiment of the invention. Shown is a retention element, specifically, a kidney retention coil 122, which has a proximal end 122p and a distal end 122d. Also shown is an elongate porous membrane delivery element 124, which has a proximal end 124p and a distal end 124d. The proximal end 122p of the kidney retention coil 122 is attached to the distal end 124d of the elongate porous membrane delivery element 124. The elongate porous membrane delivery element 124 is a tubular structure with a sealed proximal end 124p, whose width increases as one travels from the proximal end 124p to the distal end 124d. (In alternative embodiments, the width of the tubular structure may be constant along the length of the device, the width of the tubular structure may undulate along the length of the device, and so forth.) Diameter D1, the diameter of the coil, may range, for example, 1.5 to 2 cm, among other values. Length L1 may range, for example, 10 to 20 to 30 cm, among other values.

Figure 3B:
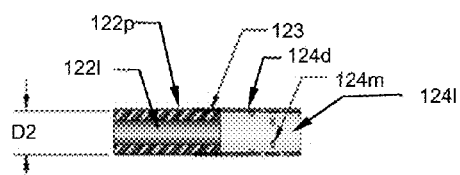
FIG. 3B is a partial cross-sectional view of the medical device of FIG. 3A, taken along plane B-B.

FIG. 3B is a partial cross-sectional view of the medical device of FIG. 3A, taken along plane B-B. This figure shows the proximal end 122d of the kidney retention coil 122 inserted into the distal end 124d of the porous membrane delivery element 124, which has numerous micropores 124m. The coil 122 has a receiving lumen 122l that extends from the distal end 122d to the proximal end 122p of the coil 122. The receiving lumen 122l is in fluid communication with an internal delivery lumen 124l of the porous membrane delivery element 124. The proximal end 122d of the coil 122 is attached and sealed to the distal end 124d of the porous membrane delivery element 124 by a bond 123, for instance a solvent bond, heat bond or adhesive bond. D2, the outside diameter of the material forming the coil 122, may range, for example, from 4 to 8 French, among other values.

Figure 4A:
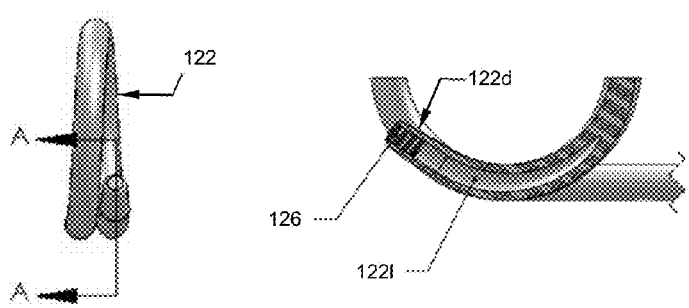
FIG. 4A is an end view of the medical device of FIG. 3A.
Figure 4B:
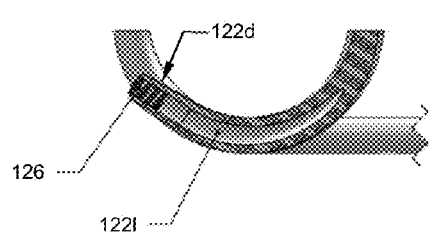
FIG. 4B is a partial cross-sectional view, taken along plane A-A of FIG. 4A.

FIG. 4A is an end view of the medical device of FIG. 3A. FIG. 4B is a partial cross-sectional view, taken along plane A-A of FIG. 4A and shows coil 122, the distal end 122d of which has an associated injection port 126. Injection port 126 may be, for instance, in the form of a polymeric material (e.g., a suitable natural or synthetic rubber material or another elastomeric material selected from the polymers listed above) that is positioned within (or over, in some embodiments) the distal end 122d of the coil 122. Injection port 126 may be attached to coil 122, for instance, by friction fit, by solvent bonding, by heat bonding or adhesive bonding, among other techniques.

An injection needle can be passed through the injection port 126 in order to deliver a urologically beneficial agent into the receiving lumen 122l of the coil 122, which acts as a receiving structure for the urologically beneficial agent. The receiving lumen 122l is in fluid communication with the internal delivery lumen 124l of the porous membrane delivery element 124, thereby allowing the urologically beneficial agent to be loaded into the porous membrane delivery element 124 via injection port 126.

Without wishing to be bound by theory, it is noted that the above-described medical device is consistent with the notion that no more than a string-like member needs to be present in a ureter in order for drainage to be maintained. The device allows a health care professional to provide one or more urologically beneficial agents by providing a self-closing injection via the injection port. The sock-like porous membrane delivery element is able to initially hold the urologically beneficial agents and to deliver the urologically beneficial agents over time.

Although not illustrated in FIGS. 3A-3B and 4A-4B, a guide wire lumen may be provided that extends through the coil, allowing the coil to be advanced into the urinary tract over a guide wire in a substantially linear configuration. Once the coil is advanced into the kidney/renal calyx, the guide wire may be removed, allowing the coil to form in the kidney. A guide wire lumen may also extend through the porous membrane delivery element as well, in some embodiments.

Although not illustrated in FIGS. 3A-3B and 4A-4B, an additional retention structure (e.g., a bladder coil) may be provided at the proximal end of the porous membrane delivery element, for instance, in order to prevent migration of the porous membrane delivery element up the ureter toward the kidney.

Figures 7A, 7B:
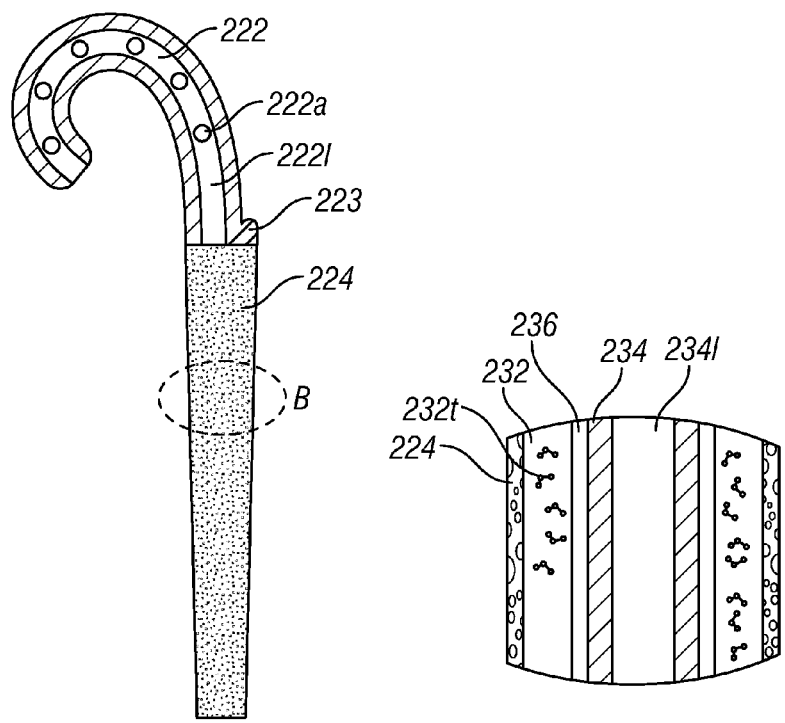
FIG. 7A is a schematic partial cross-sectional illustration of a medical device in accordance with another embodiment of the invention.
FIG. 7B is a cross-sectional view of the medical device of FIG. 7A, taken within area B.

In certain embodiments, delivery through the porous membrane delivery element is enhanced using an expandable member that acts to force the urologically beneficial agent through the porous membrane delivery element, thereby expelling the urologically beneficial from the device. In these embodiments, urine is preferably used to activate the expandable member. For instance, urine can be allowed to flow through the interior of the device whereby it is comes into contact with the expandable member, which expands and pushes the urologically beneficial agent through the porous membrane delivery element and out of the device. This will be better seen in conjunction with FIG. 7A, which is a schematic partial cross-sectional illustration of a medical device in accordance with an embodiment of the disclosure. Shown in cross-section is a kidney retention coil 222, which is hollow, having an interior lumen 222l. The kidney retention coil 222 is open at both ends and has a series of apertures 222a to assist with urine flow from the exterior of the device into the interior lumen 222l. Also shown is the exterior of a porous membrane delivery element 224 which is bonded to the kidney retention coil 222. FIG. 7B is a cross-sectional view of the porous membrane delivery element 224 of FIG. 7A, taken within area B. Referring now to this figure, there is shown a permeable tubular element 234 having an interior lumen 234l, which is in fluid communication with the interior lumen 222l of the kidney retential coil. The permeable tubular element 234 is permeable to urine that flows in its interior lumen 234l. Adjacent to the permeable tubular element 234 is an expandable region 236 which expands upon contact with urine flowing through the permeable tubular element 234. A delivery lumen 232 (which is annular in shape in the embodiment shown) containing a urologically beneficial agent 232t (which is in suspension or solution) is disposed between the expandable region 236 and the porous membrane delivery element 224. As seen in FIG. 7A, kidney retention coil 222 can be provided with a side port 223 (e.g., with a septum covered entrance) which is in fluid communication with the delivery lumen 232 and through which the delivery lumen 232 can be loaded (e.g., via a syringe). When the expandable region 236 expands upon contact with urine, it reduces the volume of the delivery lumen 232, thereby acting to increase the pressure in the delivery lumen 232, pumping the urologically beneficial agent 232 through the pores of the porous membrane delivery element 224. Passive drug elution may also occur as urine passes over the exterior of the device, coming into contact with the exterior of the porous membrane delivery element 224.

Although not illustrated in FIG. 7A, an additional retention structure (e.g., a bladder coil) may be provided at the proximal end of the porous membrane delivery element, for instance, in order to prevent migration of the porous membrane delivery element up the ureter toward the kidney.

Suitable materials for the porous membrane delivery element 224 are described above. The permeable tubular element 234 may be formed of any suitable material that is permeable to urine including metals, ceramics and polymers. In certain embodiments, the permeable tubular element 234 is a porous fluorinated polymer or copolymer (e.g., PTFE, FEP, ETFE, etc.). The expandable region 236 may be formed from any suitable material that expands upon contact with urine. Examples of such materials include urine-swellable polymeric materials which may be porous (e.g., in the form of sponge-like materials), specific examples of which include hydrophilic polymers such as polyvinyl alcohol, polyacrylic acid salts, polyacrylamides, polyethylene oxide or polyvinyl pyrrolidone, among others. The hydrophilic polymers may be crosslinked. The expandable region 236 may also be formed of a polymeric or non-polymeric osmotically active material (e.g., hydrophilic polymer, salt, sugar, etc.) enclosed in a semi-permeable membrane which allows the passage of water from the urine but does not allow passage of the osmotic material.

Where the expandable region 236 is formed of a material that may undergo expansion (swelling) upon contact with the contents of the delivery lumen 232 (e.g., urologically beneficial agent), a flexible barrier layer (e.g., impermeable polymeric layer) may be provided between the delivery lumen 232 and the expandable region 236 to prevent such contact.

Various aspects of the invention of the invention relating to the above are enumerated in the following paragraphs:

Aspect 1. An implantable or insertable urological device configured for delivery of a urologically beneficial agent into a subject, said urological device comprising (a) a porous membrane delivery element with an internal delivery lumen and (b) an injection port for introduction of a urologically beneficial agent into said delivery lumen, wherein upon implantation or insertion of said device into said subject, said urologically beneficial agent is released from the delivery lumen through pores of said porous membrane delivery element into the subject.

Aspect 2. The urological device of aspect 1, wherein the injection port is a self-closing needle injection port.

Aspect 3. The urological device of aspect 1, wherein the porous membrane has a pore size ranging from 0.1 to 10 µm.

Aspect 4. The urological device of aspect 1, wherein the porous membrane is a porous polymeric membrane.

Aspect 5. The urological device of aspect 4, wherein the porous membrane comprises expanded polytetrafluoroethylene.

Aspect 6. The urological device of aspect 1, wherein the porous membrane delivery element is an elongated structure.

Aspect 7. The urological device of aspect 6, wherein the porous membrane delivery element is in the form of an elongated tube that comprises a closed end and an opposite end that provides fluid communication with said injection port.

Aspect 8. The urological device of aspect 7, wherein a width of the elongated structure decreases with increasing distance from the injection port.

Aspect 9. The urological device of aspect 1, wherein the urological device comprises a retention element that is attached to said porous membrane delivery element.

Aspect 10. The urological device of aspect 9, wherein said retention element comprises a coil.

Aspect 11. The urological device of aspect 10, wherein said device comprises a guide wire lumen and wherein said guide wire lumen passes through said coil.

Aspect 12. The urological device of aspect 11, wherein the guide wire lumen passes through said porous membrane delivery element.

Aspect 13. The urological device of aspect 10, wherein the porous membrane delivery element is an elongate structure, and wherein the coil is attached to one end of the elongate structure.

Aspect 14. The urological device of aspect 9, wherein the retention element comprises a receiving lumen, wherein the injection port is configured to deliver the urologically beneficial agent into the receiving lumen, and wherein the receiving lumen is in fluid communication with the delivery lumen of the porous membrane delivery element.

Aspect 15. The urological device of aspect 14, wherein the retention element is in the form of a coil and wherein the receiving lumen is in the form of a coil lumen that runs through the coil.

Aspect 16. The urological device of aspect 15, wherein the injection port is disposed at one end of the coil, and wherein the porous membrane delivery element is disposed at the other end of the coil.

Aspect 17. The urological device of aspect 16, wherein the porous membrane delivery element is in the form of an elongated tube that comprises a closed end and an opposite end that provides fluid communication with the coil lumen.

Aspect 18. The urological device of aspect 16, wherein the injection port is a self-closing needle injection port.

Aspect 19. The urological device of aspect 16, further comprising a guide wire lumen that lumen extends through the coil.

Aspect 20. The urological device of aspect 19, wherein the guide wire lumen passes through said porous membrane delivery element.

Although various embodiments are specifically illustrated and described herein, it will be appreciated that modifications and variations of the present invention are covered by the above teachings and are within the purview of any appended aspects without departing from the spirit and intended scope of the invention.

The invention claimed is:

1. An implantable or insertable urological device configured for delivery of a urologically beneficial agent into a subject, said urological device comprising
   (a) a porous membrane delivery element with an internal delivery lumen,
   (b) a kidney retention element that is attached to said porous membrane delivery element, and
   (c) an injection port positioned within the kidney retention element for introduction of the urologically beneficial agent into said internal delivery lumen,
   wherein said porous membrane delivery element is in a form of an elongated tube that comprises a closed end and an opposite end that provides fluid communication with said injection port,
   wherein a width of the porous membrane delivery element increases from the closed end to the opposite end,
   wherein the internal delivery lumen is sealed off from an exterior environment, except for pores in the porous membrane delivery element through which the urologically beneficial agent is released, and
   wherein upon implantation or insertion of said device into said subject, said urologically beneficial agent is released from the internal delivery lumen through said pores of said porous membrane delivery element into the subject.

2. The urological device of claim 1, wherein the injection port is a self-closing needle injection port.

3. The urological device of claim 1, wherein the porous membrane delivery element has a pore size ranging from 0.1 to 10 µm.

4. The urological device of claim 1, wherein the porous membrane delivery element is a porous polymeric membrane.

5. The urological device of claim 4, wherein the porous polymeric membrane comprises expanded polytetrafluoroethylene.

6. The urological device of claim 1, wherein said kidney retention element comprises a coil.

7. The urological device of claim 6, wherein said device comprises a guide wire lumen and wherein said guide wire lumen passes through said coil.

8. The urological device of claim 7, wherein the guide wire lumen passes through said porous membrane delivery element.

9. The urological device of claim 6, wherein the coil is attached to one end of the elongated tube.

10. The urological device of claim 9, wherein said porous membrane delivery element has a thickness less than 100 µm.

11. The urological device of claim 1, wherein the kidney retention element comprises a receiving lumen, wherein the injection port is configured to deliver the urologically beneficial agent into the receiving lumen, and wherein the receiving lumen is in fluid communication with the internal delivery lumen of the porous membrane delivery element.

12. The urological device of claim 11, wherein the kidney retention element is in a form of a coil and wherein the receiving lumen is in a form of a coil lumen that runs through the coil.

13. The urological device of claim 12, wherein the injection port is disposed at one end of the coil, and wherein the porous membrane delivery element is disposed at another end of the coil.

14. The urological device of claim 13, wherein the injection port is a self-closing needle injection port.

15. The urological device of claim 13, further comprising a guide wire lumen that extends through the coil.

16. The urological device of claim 15, wherein the guide wire lumen passes through said porous membrane delivery element.

17. The urological device of claim 1, wherein said porous membrane delivery element has a thickness less than 100 µm.

18. The urological device of claim 1, wherein said porous membrane delivery element has a thickness less than 50 µm.

19. The urological device of claim 1, wherein said porous membrane delivery element is flexible.

\* \* \* \* \*